United States Patent
Ditter

(12) 
(10) Patent No.: US 6,231,501 B1
(45) Date of Patent: May 15, 2001

(54) URINARY OCCLUSION DEVICE

(75) Inventor: Theresa M. Ditter, Shoreview, MN (US)

(73) Assignee: Tama Medical, Inc., Long Lake, MN (US)

( * ) Notice: Subject to any disclaimer, the term of this patent is extended or adjusted under 35 U.S.C. 154(b) by 0 days.

(21) Appl. No.: 09/142,361

(22) PCT Filed: Jan. 21, 1998

(86) PCT No.: PCT/US98/01518

§ 371 Date: Sep. 4, 1998

§ 102(e) Date: Sep. 4, 1998

(87) PCT Pub. No.: WO98/32372

PCT Pub. Date: Jul. 30, 1998

Related U.S. Application Data

(60) Provisional application No. 60/036,218, filed on Jan. 28, 1997.

(51) Int. Cl.[7] .................................................. A61F 2/02
(52) U.S. Cl. .............................................................. 600/29
(58) Field of Search .................................. 128/684, 885, 128/DIG. 25; 600/29–32

(56) References Cited

U.S. PATENT DOCUMENTS

| | | | |
|---|---|---|---|
| 4,057,066 | 11/1977 | Taylor . | |
| 4,198,979 | 4/1980 | Cooney et al. . | |
| 4,822,347 | 4/1989 | MacDougall | 604/329 |
| 4,968,294 | 11/1990 | Salama | 600/30 |
| 5,030,199 | 7/1991 | Barwick et al. | 600/29 |
| 5,074,855 | 12/1991 | Rosenbluth et al. | 604/385.1 |
| 5,082,006 | 1/1992 | Jonasson | 128/885 |
| 5,090,424 | 2/1992 | Simon et al. | 128/885 |
| 5,098,379 | 3/1992 | Conway et al. | 604/51 |
| 5,114,398 * | 5/1992 | Trick et al. | 600/29 |
| 5,234,409 | 8/1993 | Goldberg et al. | 604/96 |
| 5,263,947 | 11/1993 | Kay | 604/331 |
| 5,336,208 | 8/1994 | Rosenbluth et al. | 604/329 |
| 5,352,182 | 10/1994 | Kalb et al. | 600/30 |
| 5,360,402 | 11/1994 | Conway et al. | 604/97 |
| 5,417,226 | 5/1995 | Juma | 128/885 |
| 5,476,434 | 12/1995 | Kalb et al. | 600/30 |
| 5,483,976 | 1/1996 | McLaughlin et al. | 128/885 |
| 5,509,427 | 4/1996 | Simon et al. | 128/885 |
| 5,509,889 | 4/1996 | Kalb et al. | 600/30 |
| 5,513,660 | 5/1996 | Simon et al. | 128/885 |
| 5,640,976 * | 6/1997 | Levius | 128/DIG. 25 |
| 5,662,582 * | 9/1997 | Levius et al. | 600/29 |
| 5,752,525 * | 5/1998 | Simon et al. | 600/29 X |
| 5,769,091 * | 6/1998 | Simon et al. | 128/885 |
| 5,813,974 * | 9/1998 | Guardia | 600/29 |
| 5,887,593 * | 3/1999 | Levius | 128/885 |
| 5,906,575 * | 5/1999 | Conway et al. | 600/29 |

FOREIGN PATENT DOCUMENTS

| | | |
|---|---|---|
| WO 92/19192 | 11/1992 | (WO) . |
| WO 95/08968 | 4/1995 | (WO) . |
| WO 96/00542 | 1/1996 | (WO) . |

* cited by examiner

*Primary Examiner*—Samuel G. Gilbert
(74) *Attorney, Agent, or Firm*—Crompton, Seager & Tufte LLC.

(57) ABSTRACT

This invention is a device (10) for controlling urinary incontinence in a female patient, including a shaft (12) having a length sufficient to transit the length of a female patient's urethra, a flange (16) externally extending from the shaft (12) proximate the proximal end of the shaft (12), effective for securing the shaft (12) in position within a female patient's urethra when the flange (16) is positioned between a female patient's labia minora and vestibular floor. The distal end portion of the shaft (12) is straight and free of any retention element having, or expandable to have, a diameter effective for seal engaging the urethra.

23 Claims, 10 Drawing Sheets

URINARY OCCLUSION DEVICE

CROSS REFERENCE TO A RELATED APPLICATION

The present application is a non-provisional application claiming priority to U.S. Provisional application Ser. No. 60/036,218 and a 371 of PCT/US98/01518 filed Jan. 27, 1998.

FIELD OF INVENTION

The present invention relates to devices to control and regulate urinary incontinence in women.

BACKGROUND OF THE INVENTION

Urinary incontinence in women is a relatively common problem which exists in three primary forms. Stress urinary incontinence occurs as a result of physical stress, such as lifting, coughing, or sneezing. Urge urinary incontinence is a result of gradual loss of control of the nerves that control the micturition process. Mixed urinary incontinence is a combination of symptoms of stress urinary incontinence and urge urinary incontinence.

The problem is often a source of difficulty or embarrassment to the affected woman. One solution, in relatively mild cases, has been the use of pads or diapers to absorb the uncontrolled seepage of urine. This can be undesirable as it sometimes results in restricting the type or style of clothing wished to be worn, as well as requiring frequent changing of absorbent devices. Uncomfortability and irritation due to the lingering presence of captured urine in enforced close proximity to tender urogenital tissues is another problem existing with external absorbent systems.

More severe cases require the temporary use of an intraurethral device to control the involuntary seepage or flow of urine. Several devices are known in the prior art for dealing with the problems of urinary incontinence in women. One device as claimed in U.S. Pat. No. 5,352,182, comprises a relatively rigid valved catheter having an extendible sealing portion on the interior end of the catheter. The sealing portion must be relatively rigid as it secures the device in the patient and defines at least one aperture to allow the passage of urine into the device. A manually operable valve is located between the internal and external ends of the catheter to enable the woman to selectively control elimination of urine at desired places and times. Other types of valved devices are known, and these generally comprise rigid tubular casings with valves inserted at various locations.

Still other prior art devices comprise solid plugs which are inserted into the urethra to block the involuntary seepage or flow of urine. Several such devices are known in the prior art. As claimed in U.S. Pat. No. 5,082,006, one prior art device comprises a relatively thin, solid shaft having at least one knob or thickening of the shaft along its length. Another device, as claimed in U.S. Pat. No. 5,090,424 comprises a flexible urethral plug which has a soft molded inflatable plastic catheter and a transportable fluid. The device is inserted into the urethra, and pressure applied to an external bellows which causes the fluid to be transported into the interior end of the device. The interior or distal end of the device increases in diameter as a result, securely implanting the plug on a temporary basis, until the interior or distal end of the device is deflated. Removal is then accomplished after deflation.

All known devices employ some kind of enlargement of the interior end of the catheter or shaft to secure the device within the urethra following placement. This can result in discomfort to the woman, and may lead to a sensation of a necessity to void the bladder when it may not be necessary. Additionally, many women suffering from stress urinary incontinence have bladder necks and proximal urethras that will open up during a stress event. This condition exists when the bladder neck becomes deformed from its normally perpendicular state to one which sags downward. When this condition is encountered, securing of the device via an enlarged distal end within the urethra may be negatively affected due to the enlargement occurring at the wrong position on the device. Further, all known prior art devices utilize a form stable catheter or shaft which remains temporarily implanted in the urethra As a result, the urethra will necessarily be deformed from its normally collapsed configuration which is naturally assumed at all times except during urination, when it will be open. Additional problems, such as bladder and urethral infections may also develop from the extended presence of a relatively rigid artificial body in the urethra, and associated open urethra.

What is clearly needed is a device which will allow women suffering from stress or mixed urinary incontinence to live as normal a life as possible. Such a device would ideally be secured in the urethra by means other than a thickening of the interior end, and contain a valve mechanism to allow elimination of urine from the bladder without the necessity of frequent removal followed by subsequent reimplantation of the device. Finally, such a device would comprise a thin walled and flexible catheter, so as to be able to conform as closely as possible to the natural non elimination configuration of the woman's urethra.

SUMMARY OF THE INVENTION

The present invention is directed to a device which comprises a thin walled, flexible tube which minimizes any dilatation effect on the urethra and having a length sufficient to traverse the length of the patient's urethra and into the bladder. At least the portion of the device which contacts the inner surfaces of the patient's urethra is externally coated in foam. Together, the foam and the thin flexible tube may be manufactured in three different diameter sized devices to fit the variation of diameter sizes of the urethra. These sizes would include small (14 Fr.), medium (17 Fr.), and large (20–22 Fr.) diameter sized devices. The foam serves several functions. Because of its pliable nature, it is able to be compressed with the flexible tube when under the relatively constant pressure exerted by the urethra when in the closed, non-urination configuration. Another function provided by the foam coating is that it is able to expand freely in the bladder neck, allowing it to assume the natural shape of the bladder neck. This enhances securing the device in the patient, as well as providing the additional advantage of absorbing abdominal pressure spikes during stress events. Examples of stress events are coughing, sneezing, and strenuous physical activity. Additionally, a foamed tube assuming the shape of the bladder neck creates a bottleneck effect helping to prevent the passage of urine except through the device at desired times and places for the large sized diameter devices. Or, the device offers enough obstruction to prevent leakage during a stress event but not during micturition for the small and medium sized diameter devices. Finally, a foamed tube serves to increase patient comfort during use, as well as providing a degree of structural support on the distal or internal end necessary for eventual successful elimination of urine. Extending beyond the urethra into the bladder neck is the distal portion of the device, which is provided with at least one aperture to permit the flow of urine through the device.

At the proximal end of its length, the tube is surrounded by a meatal flange which has an outer diameter which is significantly greater than that of the tube. The meatal flange helps to secure the position of the device by being normally entrapped between the labia minora and the vestibular floor. Another function of the meatal flange is to prevent migration of the device into the urethra following implantation. In one embodiment, the meatal flange comprises a relatively flat structure in another it comprises a concave structure, and in yet another, it comprises a convex structure. In the case where the meatal flange is concave towards the body, a co-axial tube may be added to direct the flow of urine that passes around the outside diameter of the urethral tube of the device through the inner diameter of the flange.

Located within the tube are valve means to enable the user to selectively eliminate urine from the bladder at an appropriate time without removing the device. This permits the user to insert the device for an extended period of time without having to remove or replace it. This would be done preferably once daily, but longer periods of implantation and use are also contemplated. An elastomeric string which is of a shorter length than the length between its point of attachment and the proximal end of the tube is attached to a stopper. The stopper is of a width sufficient to block the opening of the tube. This acts to place tension on the string and hold the stopper in place, effectively blocking the passage of urine. When an appropriate time and location for urination is reached, the user simply pulls the string to initiate urination. Other valve means are also contemplated by the invention, including an extended tube connected to a device facilitating kinking. The small and medium sized diameter devices will allow passage of urine both through the inner diameter and around the outside diameter of the urethral tube of the device. It is expected that the large sized diameter devices will only drain through the inner diameter of the urethral tube.

BRIEF DESCRIPTION OF THE DRAWINGS

It should be noted that similar structure in different embodiments of the invention are denoted by identical reference characters.

DETAILED DESCRIPTION

Figure 1:
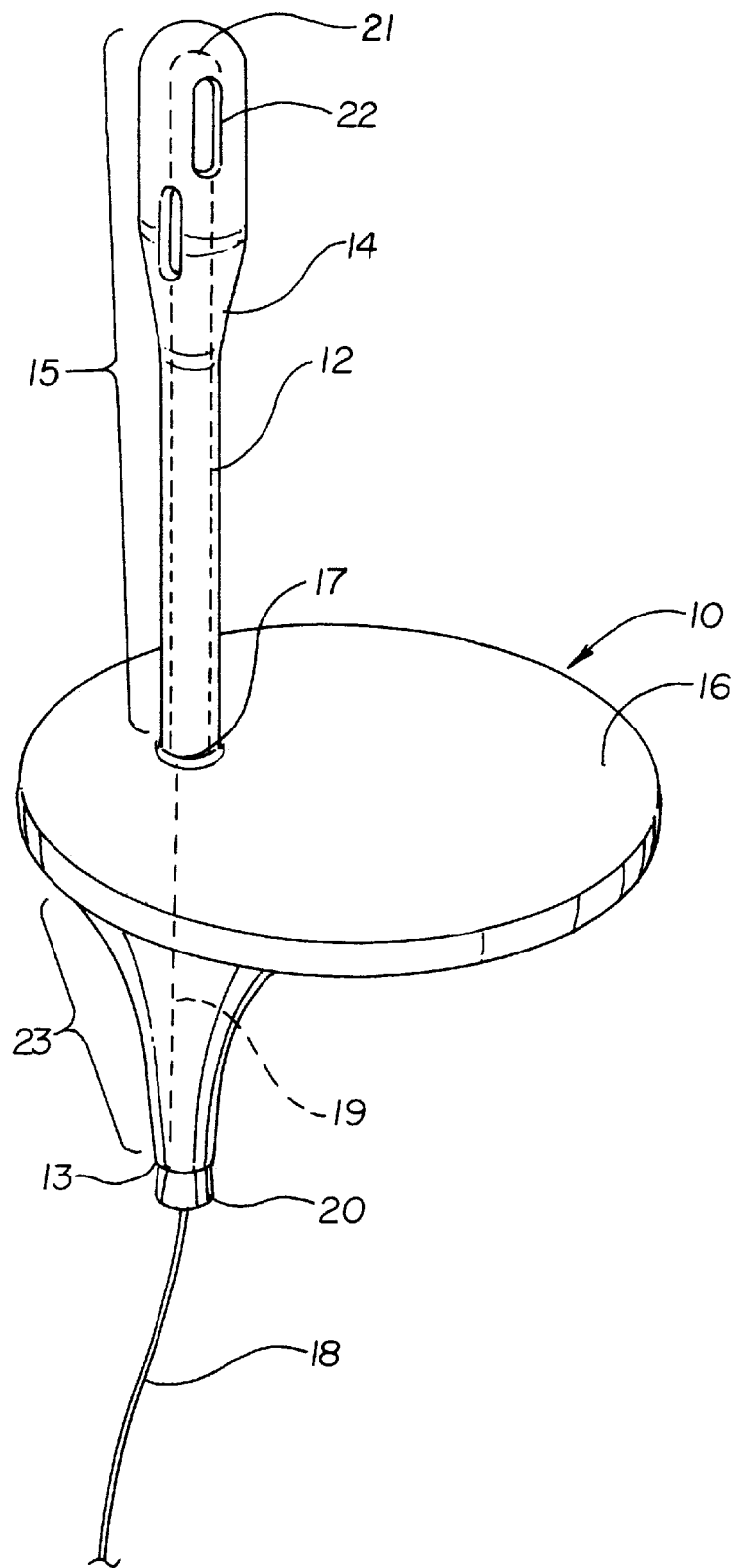
FIG. 1 is a perspective view of an embodiment of the invention having a flat meatal flange.

Nomenclature 10. female urinary occlusive insert
12. tube
13. exit point of flange
14. foam on outside of tube
15. length of tube
16. meatal flange
17. attachment point of elastomeric string
18. pull string
19. elastomeric string connecting stopper to flange
20. stopper
21. soft foam tip on distal end
22. holes in distal end of tube
23. flange extension
24. insertion tool
26. upward concave meatal flange
36. downward concave meatal flange
40. kinking valved alternative embodiment of female urinary occlusive insert
42. kinking clamp
46. flange of kinking valved embodiment of insertion
50. upward concave embodiment of flange
60. downward concave embodiment of flange
61. flange drainage hole
62. co-axial tube attached to the flange extension
63. attachment string
64. rim of flange Construction and Use The present invention is a device designed to treat urinary incontinence in women.

FIG. 1 shows an embodiment of the invention, which is generally shown at 10, having a flexible tube 12 mounted in and attached to a meatal flange 16 in an off center and substantially perpendicular manner. At least the portion of the tube 12 extending distally from the meatal flange 16 is coated with foam 14, but alternatively the entire tube 12 and/or meatal flange 16 may also be coated with foam 14. The distal end 21 of the tube 12 is closed and rounded in configuration and coated with foam 14, to provide enhanced comfort and safety to the user. It is contemplated that some of the devices will have the distal end 21 of the tube 12 be coated with a thicker layer of foam than is the length 15 of the tube 12. In typical situations, the outside diameter will be approximately 17 French( 5.7 mm) along the length of the tube 15, to approximately 19 French (6.3 mm) at the distal end 21. Proximally from the distal end of the tube 12 is at least one and preferably two or more openings 22 passing through both foam 14 and tube 12, to permit the passage of urine, which accumulates in the bladder, through the device 10, for eventual elimination. At the proximal end 13 of the flange extension 23 is a stopper 20, which is attached to the device 10 by an elastomeric string 19. The elastomeric string 19 is of a length shorter than the distance between its attachment point 17 on the meatal flange 16 and the proximal end 13 of the flange extension 23. With the stopper 20 attached, this stretches the elastomeric string 19, thus placing tension on the stopper 20, and serving as a valve mechanism to prevent the flow of urine from the device at unintended times and places. A pull string 18 is attached to the stopper 20 to be able to initiate and control the urination process.

The tube 12 is preferably made of a material possessing the characteristics of good strength, flexibility, and biocompatibility. It should be strong enough to withstand the stresses involved in insertion and withdrawal, as well as the stresses imposed upon it required by repeated usage of the valve mechanism. It is critical that the tube 12 be flexible enough to be partially collapsed or flattened by the pressure exerted on it by the normal action of the closed urethra. Acceptable materials for the tube 12 include, but are not limited to, polyurethane, silicone, "PEBAX"®, "C-FLEX"®, "PTFE, "TECOFLEX"®, "Tecothane"®, and "Pellathane"®.

Tube 12 is coated with a foam material 14. The presence of foam 14 on the outer surfaces of the tube is sufficiently flexible to be compressed by the normal internal pressure exerted by the urethra in the closed, non-urination configuration. Thus, following insertion, the foam may compress in the urethra to conform as closely as possible to the normal shape of the urethra in the non-voiding state, giving maximum comfort. The foam is also space filling to prevent unwanted leakage of urine. Yet another effect of the foam 14 coating the tube 12 is that after insertion the portion of the foamed 14 tube 12 extending into the bladder neck is able to freely expand, thus automatically assuming the shape of the bladder neck. This phenomenon, in turn, provides several additional advantages. When dealing with stress incontinence, stresses are exerted on the bladder, causing inadvertent urination. The presence of expanded foam over a flexible tube within the bladder neck and assuming the shape of the bladder neck serves to reduce the effects of stress incontinence by absorbing abdominal pressure spikes during stress events. Such events include coughing, sneezing, and other vigorous physical activity. Additionally the expanded foam creates a bottleneck effect, effectively enhancing sealing of the device and resisting the passage of urine through the urethra.

Foam materials should be of the open-cell type, and may or may not exhibit some swelling due to absorption of ambient body moisture. Where foam materials exhibiting swelling characteristics are used, the device has improved retention characteristics following emplacement. The foam material must also remain soft and flexible enough to provide patient comfort, as well as exhibiting good biocompatibility characteristics. It is contemplated to combine or coat the foam with an anti-microbial chemical agent with the foam such as chlorhexidine gluconate (CHG) or silver compounds to reduce the likelihood of infection during use. Additionally, materials such as hyaluronic acid a hydrogel or other materials may be impregnated in or coated on the foam to mimic mucous. A slip coat such as a hydrophilic hydrogel or a hydrophobic silicone may be applied to the foam to facilitate insertion and removal. Suitable foam materials include silicone, polyurethane, polyvinyl acetal polymer (PVA), and polyvinyl formyl sponge.

It is further contemplated that adhesive materials may be applied to the outer surface of the meatal flange 16 to aid in securing the device after emplacement. Suitable adhesive materials include a hydrogel and a hydrocolloid material.

It will be appreciated that a wide variation in urethral size exists in different women. Accordingly, it is required that a size range in the outer dimensions of the insertion portion (i.e., the tube 12 with its outer coating of foam 14) is required to accommodate this variation. It is contemplated that this requires an outer diameter range from approximately 12 French (4.0 mm) to 26 French (8.7 mm). It will be understood, however, that in unusual cases, this range is likely to be exceeded in either direction. Therefore, the dimensional figures given are for purposes of illustration only and not intended to be limiting.

Flange 16 is made of a medical grade aliphatic polyurethane sold commercially under the name "TECOFLEX"®. Stopper 20, as well as elastomeric string 19 will be made a of medical grade silicone or urethane.

Figure 2:
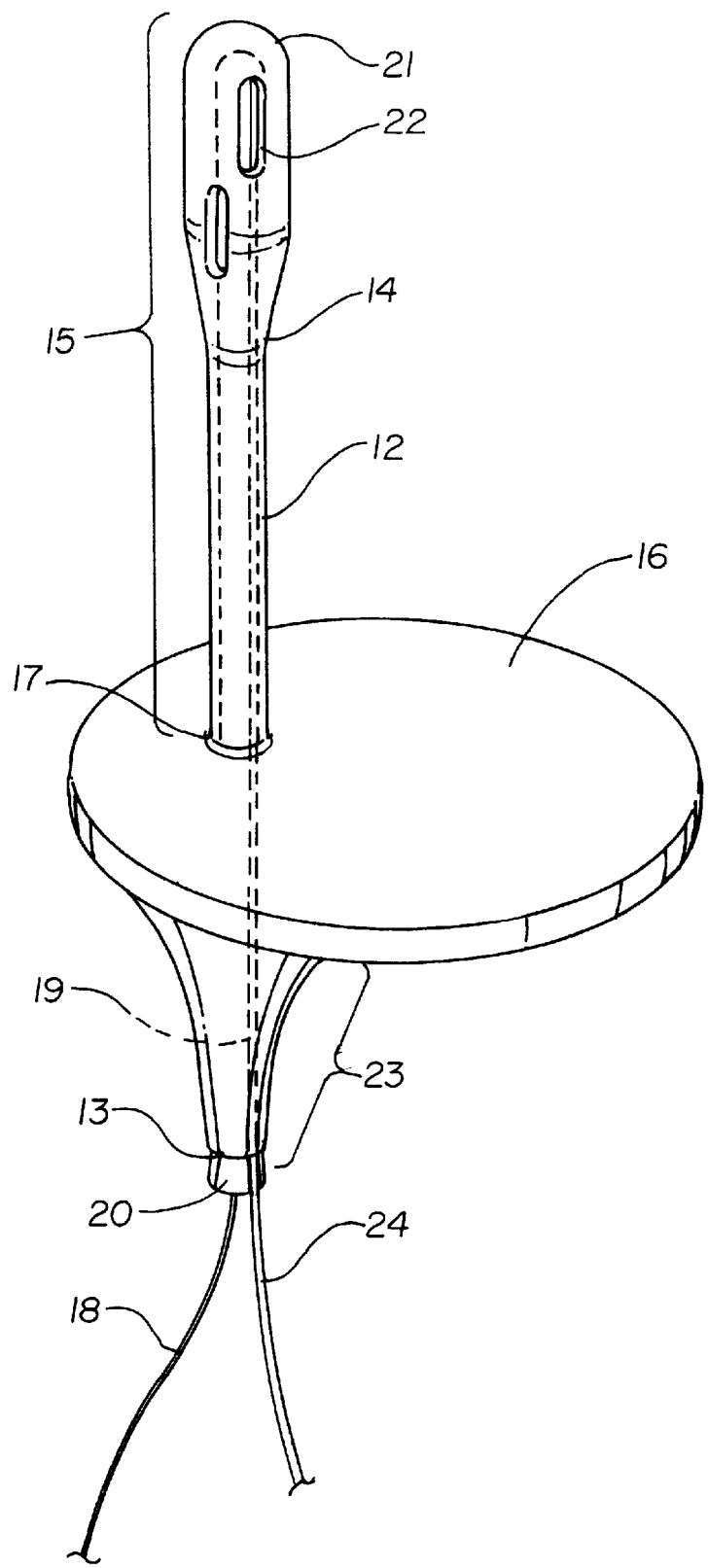
FIG. 2 is a perspective view of the embodiment of FIG. 1, with the introducer tool placed in the device, ready for implantation into the patient.

FIG. 2 shows the device 10 of the embodiment shown in FIG. 1 with an introducer tool 24 in place and extending the length of the tube 12. The introducer tool 24 is comprised of a relatively stiff material such as nylon, and is of a smaller outer diameter than the inner diameter of the tube 12. At the far distal end of the introducer tool 24, the tool is rounded to minimize the likelihood of penetrating the closed distal end 21 of the tube 12 during insertion. The device 10 is sold sterilized with the introducer tool 24 preloaded.

Figure 10:
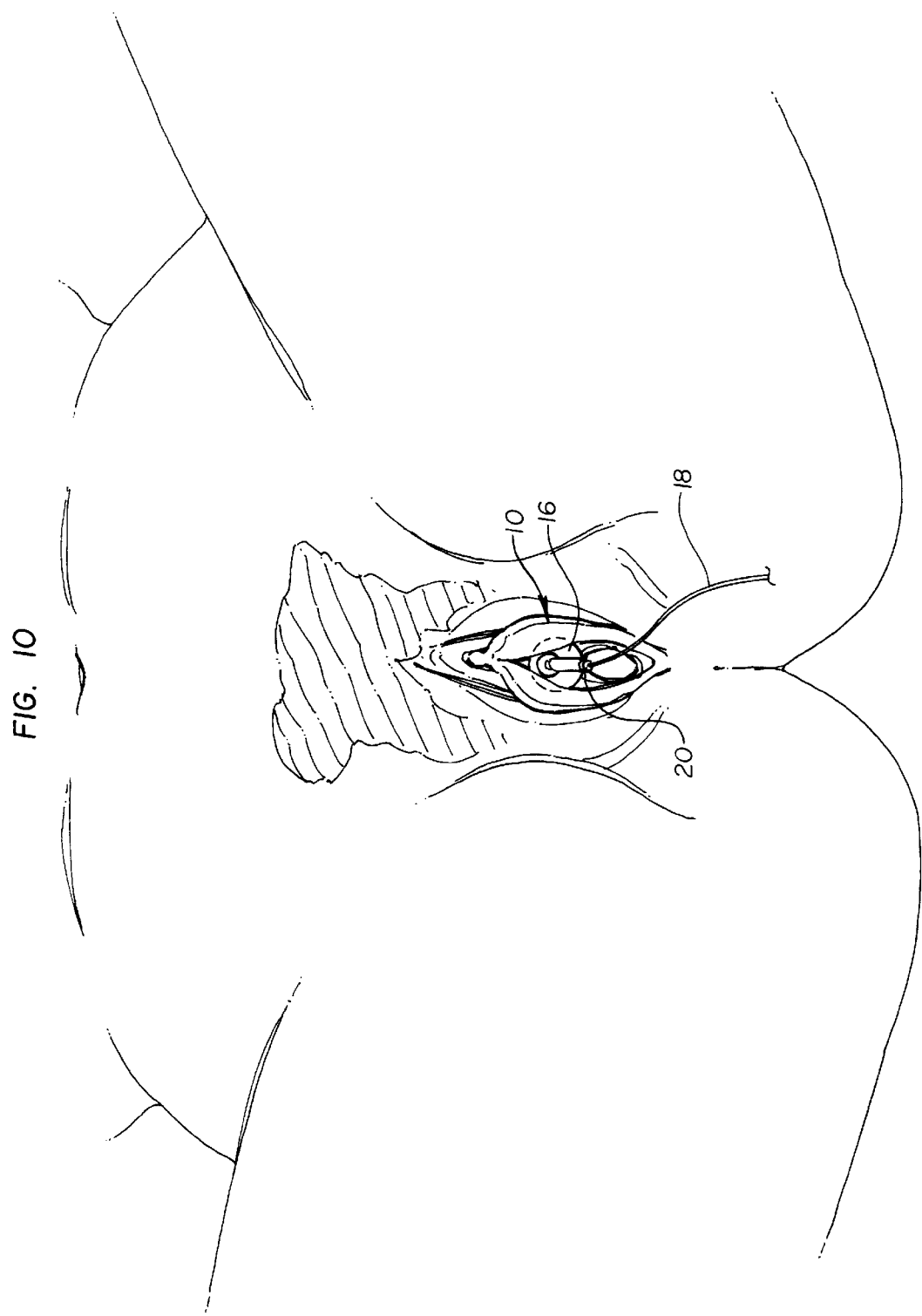
FIG. 10 shows emplacement of the invention into a female with the labia majora open and the labia minora flapping over the meatal flange.
Figure 11:
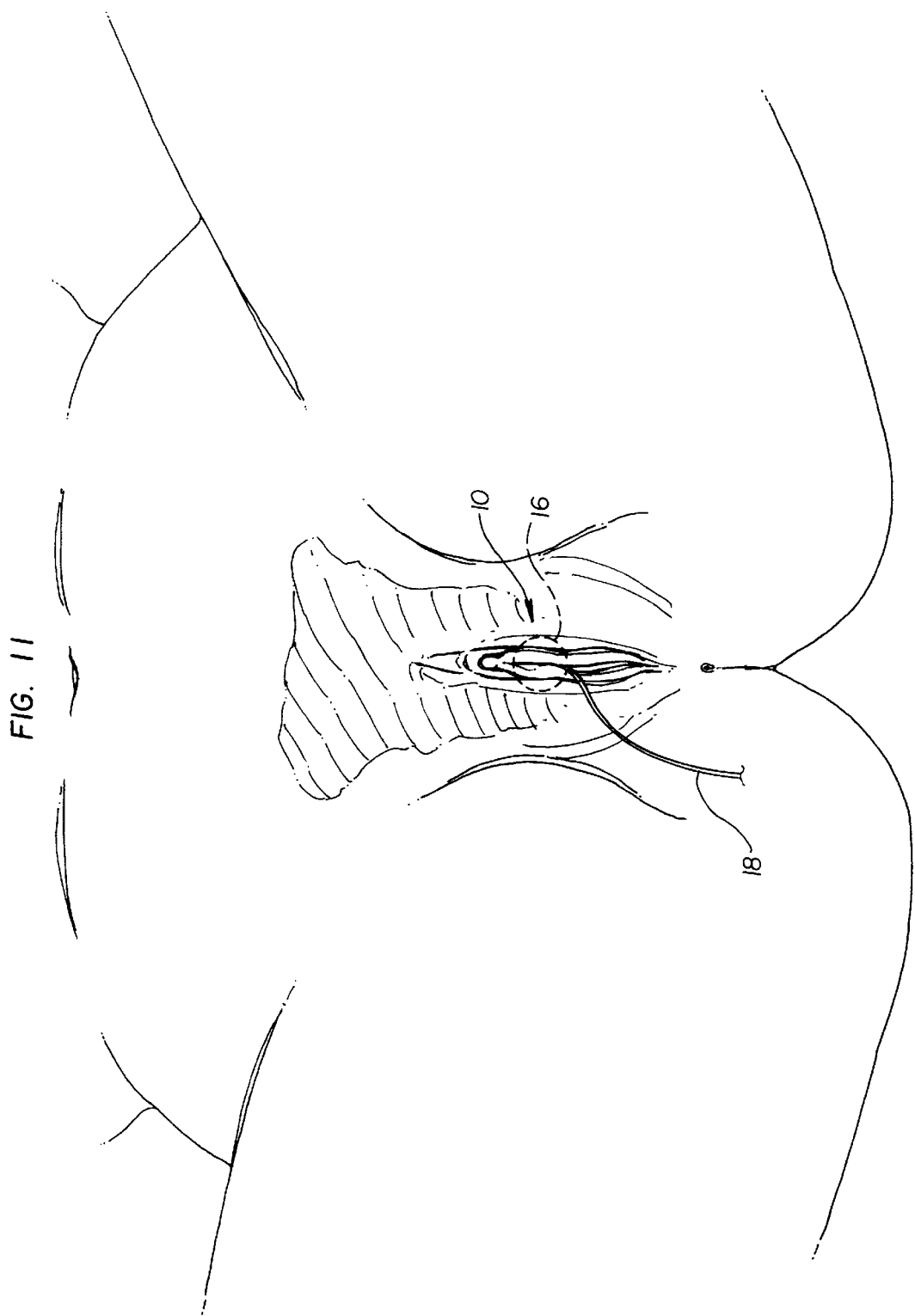
FIG. 11 shows placement of the invention into a female following insertion and held in place by the meatal flange being behind the closed labia majora and labia minora.

Insertion of the device can be done by the user. The device is intended to be replaced on a daily basis. As best shown in FIG. 10, the patient first spreads or opens her labia majora and labia minora to expose the urethral orifice. The device is inserted into the patient's urethral orifice until the meatal flange 16 rests against the vestibular floor or meatus. As best illustrated in FIG. 11, when the device is fully inserted, the labia majora and labia minora are allowed to close, covering the meatal flange 16, and firmly securing the device 10 throughout the period of use. Following emplacement of the device 10, the introducer tool 24 is removed. When it is necessary for the patient to urinate, the patient locates and pulls the pull string 18, which may extend externally from the meatus, attached to the stopper 20 with one hand while securing the device with the other hand to initiate the flow of urine from the bladder. Following successful urination, the pull string 18 and stopper 20 are allowed to return to the closed position, where the flow of urine is again prevented. Thus, removal is accomplished by the patient spreading or opening her labia majora and labia minora, and simply withdrawing the device. In the case of a thicker foam coating 14 on the distal end 21 of the device, the material is very soft and pliant, which allows any retained moisture to be easily squeezed out. Removal of the device therefore, results in compression of the thickened foam on the distal end 21, allowing easy removal.

Figure 3:
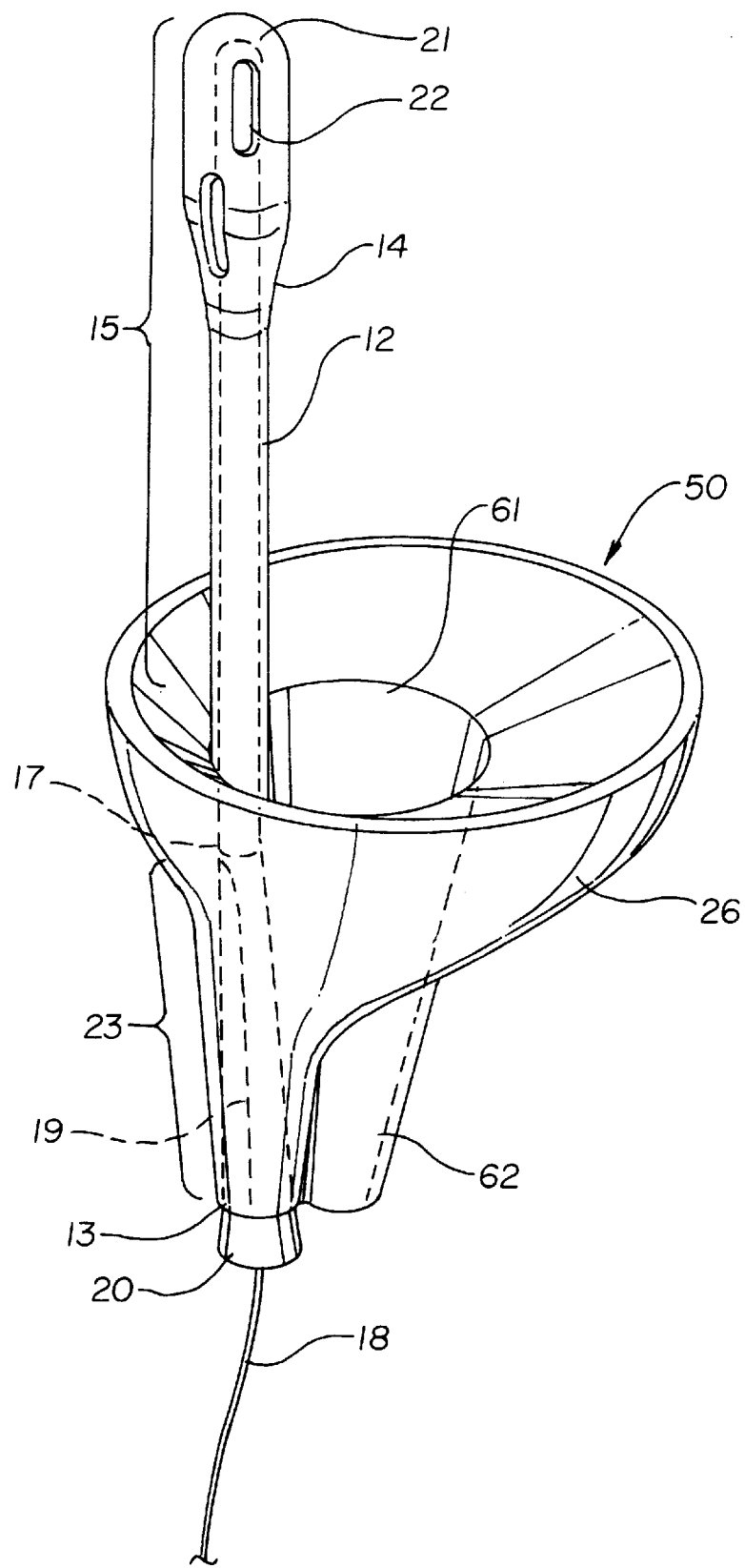
FIG. 3 is a perspective view of a further embodiment of the invention having a concave shaped meatal flange, the concavity being in the direction toward the direction of insertion into the patient's urethra.

FIG. 3 shows a particularly preferred embodiment of the invention generally indicated at 50, having a meatal flange 26 in a concave form, with the concavity toward the direction of insertion into the patient's urethra. In this embodiment the concavity of the meatal flange 26 serves to further secure the device 50 in position by creating a degree of suction between the flange 26 and labia minora of the patient. The concavity may contain a hydrogel or hydrocolloid adhesive to aid in sealing and retainment. This embodiment contains a drainage hole 61 in the flange 26 with a co-axial tube 62 attached to the flange extension 23 permitting drainage of urine flowing outside the tube 12 to drain through the inner diameter of the flange 26 thus preventing the user from wetting the hands with urine. In all other aspects, it is similar with the embodiment shown in FIGS. 1 and 2.

Figure 4:
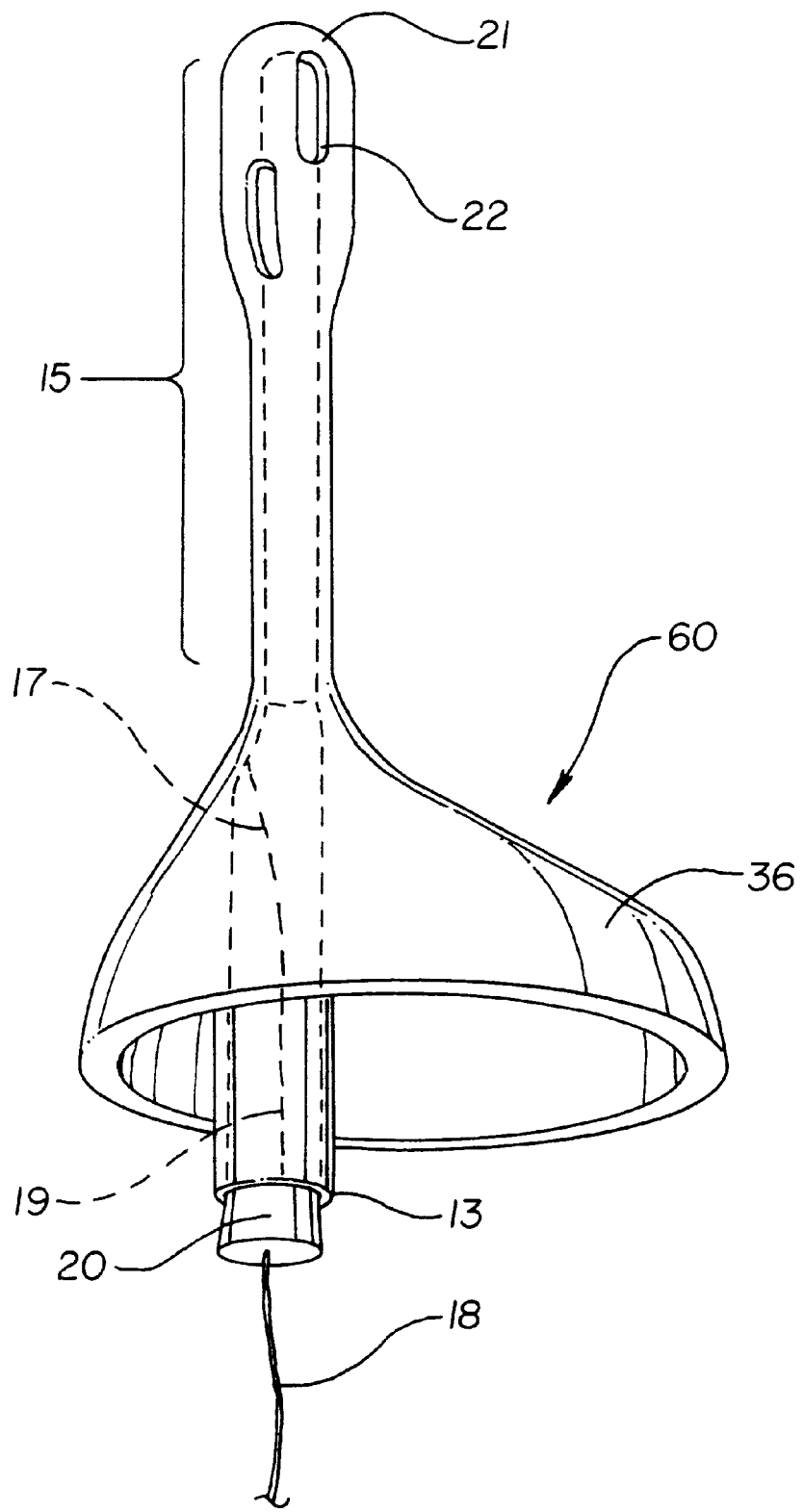
FIG. 4 is a perspective view of still another embodiment of the invention having a concave shaped meatal flange, the concavity being in the direction away from the direction of insertion into the patient's urethra.

FIG. 4 shows another embodiment of the invention generally indicated at 60 having a meatal flange 36 in a concave form, with the concavity away from the direction of insertion of the patient's urethra. In this embodiment, the concavity of the flange 36 facing in an outward direction and being between the vestibular floor and labia majora and labia minora, helps to seal the device in cases where a small amount of urine leakage occurs. It is contemplated that this embodiment of the device could be used with or without an adhesive to facilitate securing.

Figure 5:
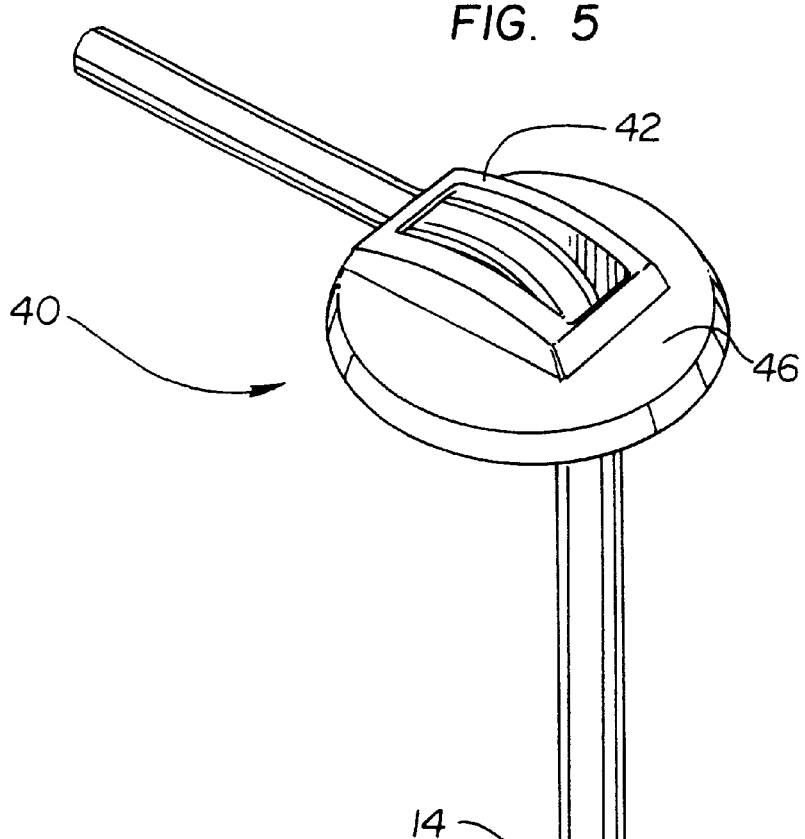
FIG. 5 is a perspective view of an alternative embodiment of the invention having a device for kinking the tube mounted on the meatal flange.
Figure 6:
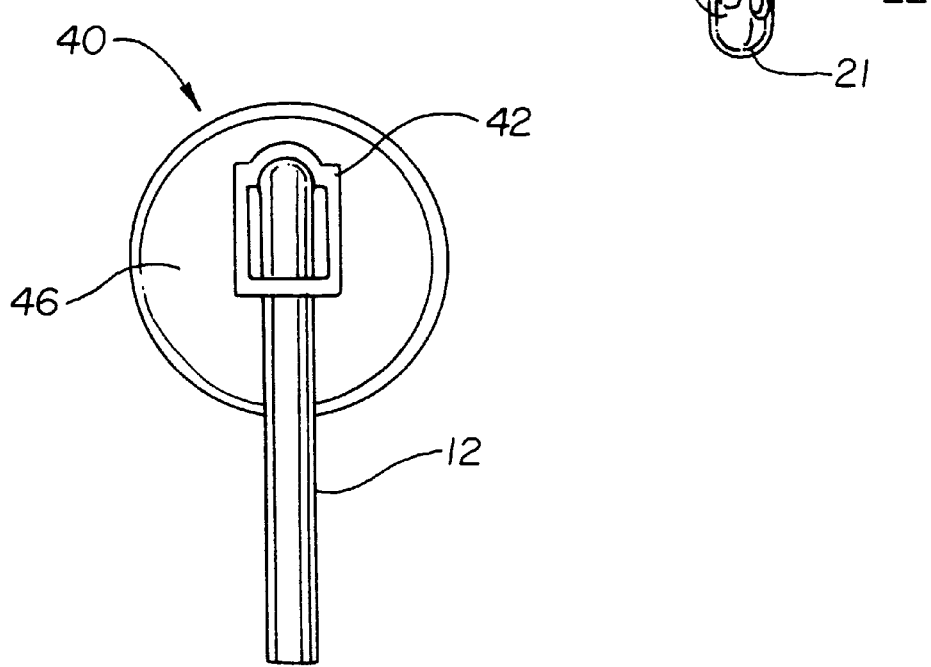
FIG. 6 is an end view of the embodiment of the invention shown in FIG. 5.
Figure 7:
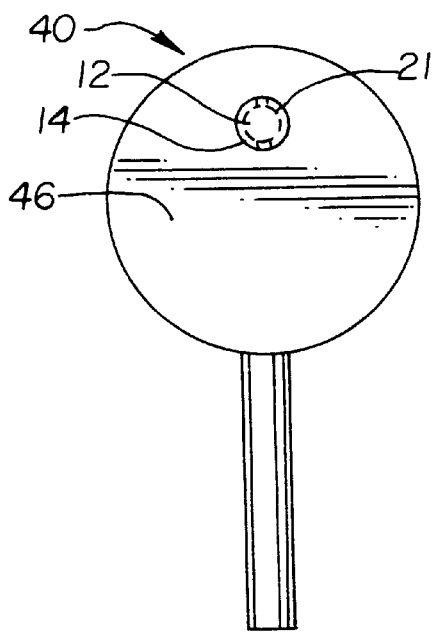
FIG. 7 is an opposite end view of the embodiment of the invention shown in FIG. 5.
Figure 8:
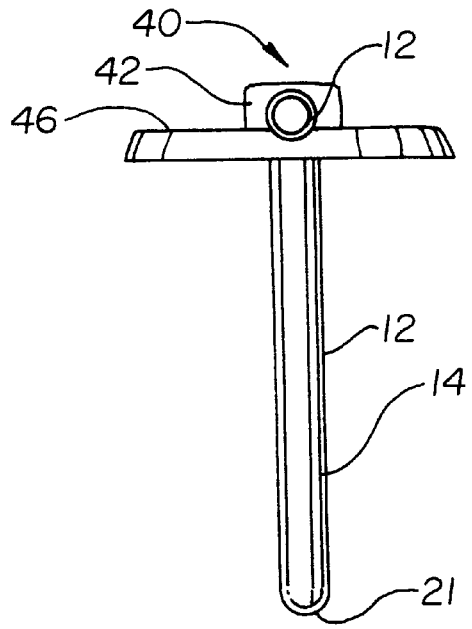
FIG. 8 is a underside view of the embodiment of the invention shown in FIG. 5.
Figure 9:
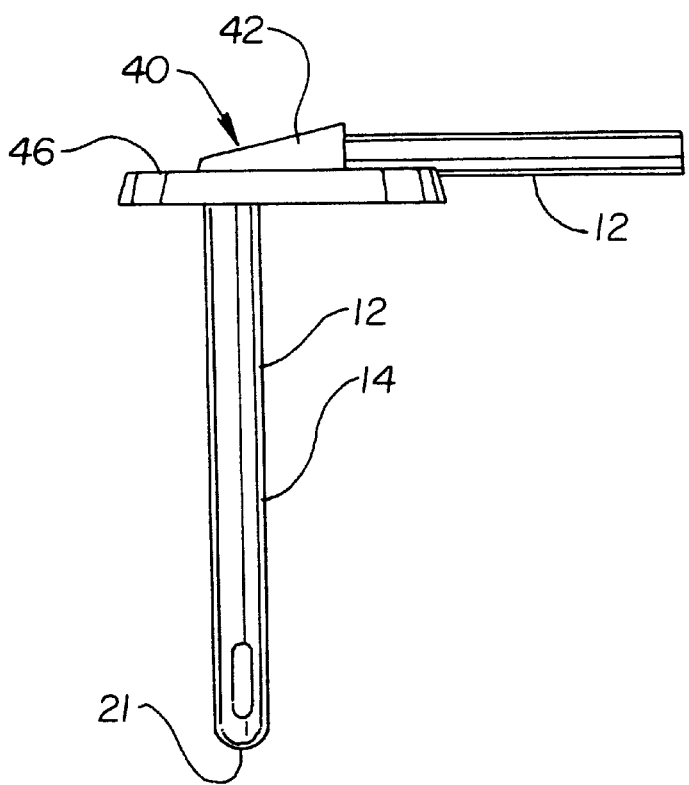
FIG. 9 is a side view of the embodiment of the invention shown in FIG. 5.

FIG. 5 shows an alternative embodiment of the invention having a kinking type valve mechanism for controlling the flow of urine. The device is generally indicated at 40 and comprises an extended flexible tube 12 which passes through a meatal flange 46 at an off-center position. At least the portion of the tube 12 which extends distally from the meatal flange 46 in the direction of eventual insertion into the patient is covered with foam 14. The distal end of the tube 21 is closed and rounded and covered by foam 14 to provide an enhanced measure of comfort and safety to the patient. On the proximal side of the meatal flange 46 is provided a kinking clamp 42, through which the tube 12 passes and is secured to. In its normal configuration, the kinking clamp 42 parallels the surface plane of the meatal flange 46, which effectively kinks the tube 12, acting as a valve mechanism. This enables the user to be able to control the time and location of urination. In its method of usage, the embodiment of FIG. 5 is identical to the embodiments shown in FIGS. 1, 3 and 4.

FIGS. 6–9 show different views of the embodiment of FIG. 5.

Figure 12:
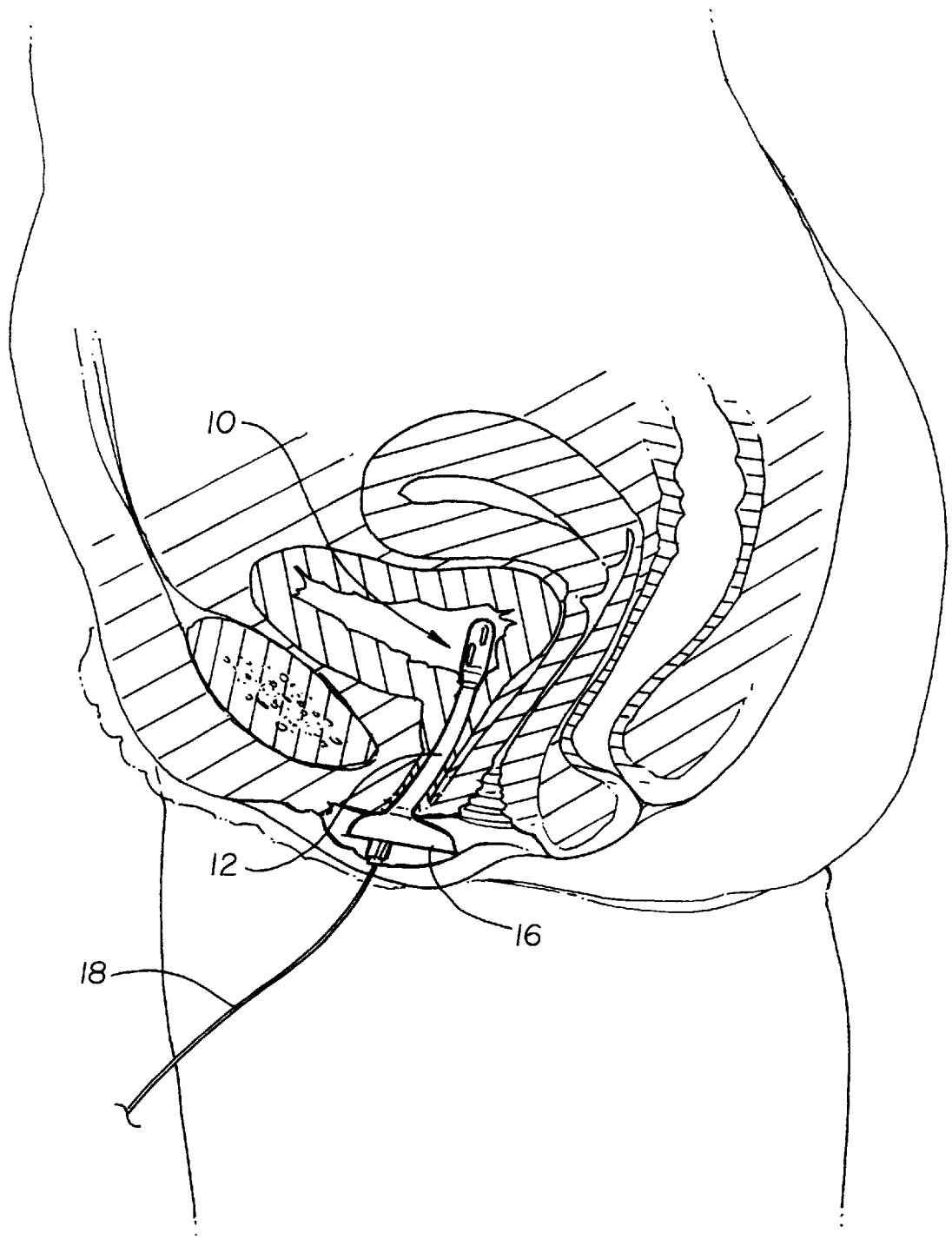
FIG. 12 is a side view showing the invention placed in the urethra of a female with the female body being shown in cross section.

FIG. 12 shows a side view of the invention as used by being placed in the urethra of a female, with the female body being shown in cross section. It can be seen that the pull string 18 protrudes from the woman's labia majora to activate the valve mechanism.

Although the invention has been described in considerable detail with reference to certain preferred versions thereof, other versions are possible. For example, different types of valve mechanisms can be employed. Therefore, the spirit of the appended claims should not be limited to the description of the preferred embodiments contained herein.

Figure 13:
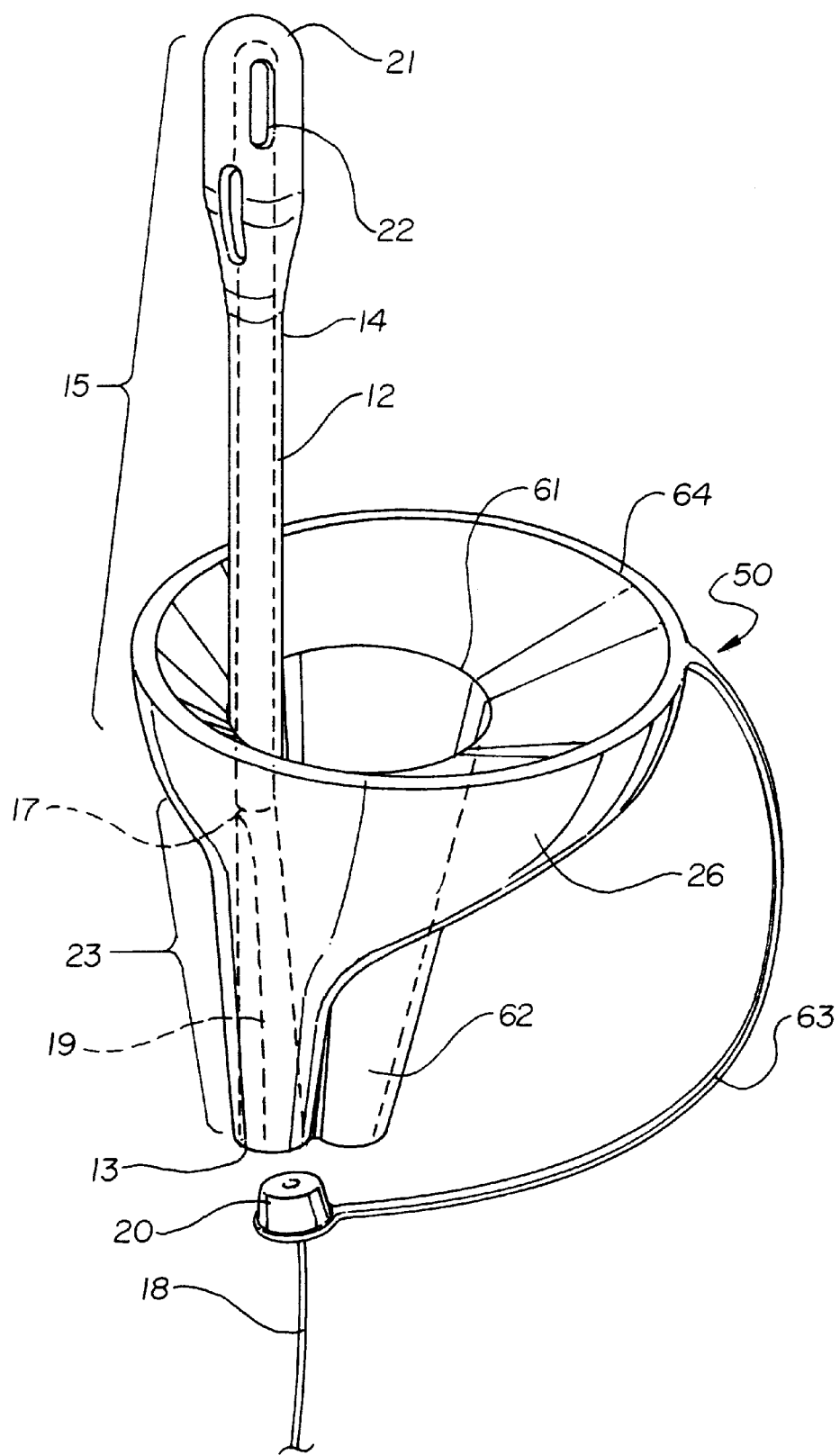
FIG. 13 shows another embodiment of FIG. 3 but with the stopper attached externally to the rim of the flange.

FIG. 13 is another embodiment of FIG. 3 but with a different stopper arrangement. The stopper is now attached by a string 63 externally to the rim 64 of the flange 26. The stopper 20 can still be removed from the exit point of the flange 13 with a pull string 18.

I claim:

1. A device for controlling urinary incontinence in a female patient, comprising:
   (a) a shaft having an external diameter, a proximal end, a distal end, and a length; and
   (b) a flange externally extending from the shaft proximate the proximal end of the shaft, effective for securing the shaft in position within a female patient's urethra when the flange is positioned between a female patient's labia minora and vestibular floor, the flange defining a passage;
   (c) wherein a distal end portion of the shaft is substantially straight and possesses a diameter such that the diameter of the urethra during micturition is sufficiently greater than the diameter of the shaft to prevent sealingly engaging the urethra, but sufficiently small relative to the diameter of the shaft to cause a sealing engagement of the urethra at all times other than during micturition.

2. The device of claim 1 wherein the shaft is a tube having an internal channel extending from a first opening proximate the distal end of the tube to a second opening proximate the proximal end of the tube between the external flange and the proximate end of the tube.

3. The device of claim 2 further comprising a valve within the internal channel proximate the proximal end of the tube for selectively controlling the flow of urine through the internal channel.

4. The device of claim 3 wherein the valve comprises (i) a stopper configured and arranged to sealingly engage the second opening in the tube, and (ii) a biasing means biasing the stopper towards sealing engagement within the second opening 5. The device of claim 3 wherein the valve comprises (i) a stopper configured and arranged to sealingly engage the second opening in the tube, and (ii) a retaining means connecting the stopper to the flange so as to maintain physical connection between the stopper and the device when the stopper is removed from the second opening.

6. The device of claim 1 wherein the shaft has an intermediate portion between the distal end of the shaft and the external flange constructed from a material that is pliable upon the application of a human force.

7. The device of claim 6 wherein said shaft is flexible.

8. The device of claim 6 wherein the pliable material is a material capable of swelling when infused with urine.

9. The device of claim 8 wherein the pliable material has a radial thickness, and the radial thickness of the pliable material proximate the distal end of the shaft is greater than the radial thickness of the pliable material proximate the proximal end of the shaft.

10. The device of claim 1 wherein the flange is concavo-convex with a concave surface facing the distal end of the shaft.

11. The device of claim 1 wherein the flange has a concave surface facing the proximal end of the shaft.

12. A device for controlling urinary incontinence in a female patient, comprising:
   (a) a shaft having an external diameter of greater than about 12 and less than 17 French, such that the diameter of the urethra during micturition is sufficiently greater than the diameter of the shaft to prevent sealingly engaging the urethra, but sufficiently small relative to the diameter of the shaft to cause a sealing engagement of the urethra at all times other than during micturition, a proximal end, a distal end, and a length; and
   (b) a flange externally extending from the shaft proximate the proximal end of the shaft, effective for securing the shaft in position within a female patient's urethra when the flange is positioned between a female patient's labia minora and vestibular floor the flange defining a passage.

13. The device of claim 12 wherein the shaft has an intermediate portion between the distal end of the shaft and the external flange constructed from a material that is pliable upon the application of a human force.

14. The device of claim 13 wherein said shaft is flexible.

15. A device for controlling urinary incontinence in a female patient, comprising:
   (a) a shaft having an external diameter, such that the diameter of the urethra during micturition is sufficiently greater than the diameter of the shaft to prevent sealingly engaging the urethra, but sufficiently small relative to the diameter of the shaft to cause a sealing engagement of the urethra at all times other than during micturition, a proximal end, a distal end, and a length; and (b) a flange externally extending from the shaft proximate the proximal end of the shaft and having a concave surface facing the distal end of the shaft, the flange defining a passage; the flange effective for (i) securing the shaft in position within a female patient's labia minora and vestibular floor and (ii) channeling urine voided around the outside of the shaft to the passage when the shaft is inserted within a female patient's urethra.

16. The device of claim 15 wherein the shaft has an intermediate portion between the distal end of the shaft and the external flange constructed from a material that is pliable upon the application of a human force.

17. The device of claim 15 wherein the tube extends off-center through the flange.

18. The device of claim 15 further comprising a drainage hole extending through the flange effective for draining urine collected by the flange towards the distal end of the shaft.

19. A method for controlling incontinence in a female patient, comprising:

(a) selecting a device, comprising:
   (i) a shaft of substantially uniform external diameter having a proximal end, a distal end and a length; and
   (ii) a flange externally extending from the shaft proximate the proximal end of the shaft, effective for securing the shaft in position within a female patient's urethra when the flange is positioned between a female patient's labia minora and vestibular floor, the flange defining a passage;
   (iii) wherein the shaft has a length sufficient to transit the length of the female patient's urethra, and an external diameter effective for restricting the flow of urine through the female patient's urethra during a stress event, while permitting the flow of urine between the tube and the urethra during micturition; and (b) inserting the shaft into the female patient's urethra so as to position the distal end of the shaft proximate the female patient's bladder and the flange between the female patient's labia minora and vestibular floor.

20. The method of claim 19 wherein (i) the shaft is a flexible tube, (ii) the tube has an internal channel extending from a first opening proximate the distal end of the tube to a second opening proximate the proximal end of the tube between the external flange and the proximate end of the tube, and (iii) the method further comprises inserting a rigid elongated tool into the internal channel through the second opening before the tube is inserted into the female patient's urethra, and withdrawing the tool from the internal channel after the tube has been fully inserted into the female patient's urethra.

21. The method of claim 19 wherein (i) the flange has a concave surface facing the distal end of the shaft defining a concavity effective for collecting urine voided around the outside of the shaft when the shaft is inserted within the urethra of a female patient, and (ii) the device further comprises a drainage hole extending through the flange effective for draining urine in the concavity towards the distal end of the tube.

22. A method for controlling incontinence in a female patient with an occlusionary device without requiring removal of the occlusionary device to void, comprising:

(a) selecting a female urinary occlusion device, comprising:
   (i) a shaft having an external diameter, a proximal end, a distal end and a length;
   (ii) a flange externally extending from the shaft proximate the proximal end of the shaft, effective for securing the shaft in position within a female patient's urethra when the flange is positioned between a female patient's labia minora and vestibular floor; and
   (iii) the flange defining a passage effective for draining urine collected by the flange towards the distal end of the shaft;

(b) inserting the shaft into the female patient's urethra so as to position the distal end of the shaft proximate the female patient's bladder and the flange between the female patient's labia minora and vestibular floor; and (c) permitting the female patient to urinate with the device inserted within the urethra, whereby urine flows around the inserted shaft and through the opening in the flange.

23. The method of claim 22 further comprising replacing an inserted device with a fresh device daily.

* * * * *